(12) United States Patent
Brossia et al.

(10) Patent No.: US 6,911,828 B1
(45) Date of Patent: Jun. 28, 2005

(54) APPARATUS AND METHOD FOR DETECTING THE DEGRADATION OF A COATING USING EMBEDDED SENSORS

(75) Inventors: Christopher S. Brossia, San Antonio, TX (US); Darrell S. Dunn, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 308 days.

(21) Appl. No.: 10/153,996

(22) Filed: May 23, 2002

Related U.S. Application Data

(60) Provisional application No. 60/293,295, filed on May 23, 2001.

(51) Int. Cl.$^7$ ............................................. G01R 27/28
(52) U.S. Cl. ..................................... 324/649; 324/663
(58) Field of Search ................................. 324/649, 663

(56) References Cited

U.S. PATENT DOCUMENTS

| | | | |
|---|---|---|---|
| 3,357,237 A | 12/1967 | Le Bel | |
| 3,782,181 A | 1/1974 | Gurtler | |
| 4,839,593 A | 6/1989 | Spies | |
| 5,286,357 A * | 2/1994 | Smart et al. | 205/776 |
| 5,698,085 A | 12/1997 | Yu | |
| 5,746,905 A | 5/1998 | Murray | |
| 5,859,537 A | 1/1999 | Davis | |
| 6,004,396 A | 12/1999 | Ishikawa | |
| 6,052,517 A | 4/2000 | Matsunaga | |
| 6,195,789 B1 | 2/2001 | Matsunaga | |
| 6,208,128 B1 | 3/2001 | Braconnier | |
| 6,248,184 B1 * | 6/2001 | Dull et al. | 148/275 |
| 6,313,646 B1 * | 11/2001 | Davis et al. | 324/690 |
| 6,328,878 B1 * | 12/2001 | Davis et al. | 205/776.5 |
| 6,693,417 B2 * | 2/2004 | Wilson | 324/158.1 |
| 2002/0057097 A1 * | 5/2002 | Kelly et al. | 324/700 |
| 2002/0154029 A1 * | 10/2002 | Watters et al. | 340/870.07 |
| 2002/0190729 A1 * | 12/2002 | Wilson | 324/663 |
| 2004/0118682 A1 * | 6/2004 | Murray et al. | 204/418 |

* cited by examiner

Primary Examiner—Charles H. Nolan, Jr.
(74) Attorney, Agent, or Firm—Kammer Browning PLLC

(57) ABSTRACT

A system and method for monitoring the effectiveness of a coating on a substrate surface and indicating the failure of the coating to adequately protect the surface from corrosion, degradation, and the like. The system includes a sensor array positioned in contact with the coating utilizing a number of sensor electrodes connected to a single integrated circuit or a number of separate individual sensor circuits. The electrodes of the sensor array make measurements of the electrochemical impedance characteristics of the coating and provide such data by way of telemetry to a data interrogation device that is periodically be placed in proximity to the sensor array. The interrogation device may serve to both power the sensor array and trigger it to acquire data. A nominal parameter N', which is the product of the impedance magnitude and the phase angle, is utilized as a direct indication of the resistance and capacitance characteristics of the coating and therefore a direct indication of the coatings effectiveness.

30 Claims, 4 Drawing Sheets

APPARATUS AND METHOD FOR DETECTING THE DEGRADATION OF A COATING USING EMBEDDED SENSORS

This application claims the benefit of provisional application 60/293,295 filed May 23, 2001.

BACKGROUND OF THE INVENTION

1. Field of Invention

The present invention relates, in general, to the field of corrosion sensing and monitoring. More specifically, the present invention provides a system and a method to monitor the condition of a protective coating (e.g., paint) on a substrate and to detect degradation in the protectiveness of the coating prior to the onset of substrate corrosion.

2. Description of the Related Art

Atmospheric corrosion of steels, aluminum alloys, and Al-clad aluminum alloys is a problem for many civil engineering structures, commercial and military vehicles, and aircraft. Paint is usually the primary means to prevent the corrosion of steel bridge components, automobiles, trucks, and aircraft. Under ideal conditions, the coating provides a continuous layer that is impervious to moisture. The ability of a coating to provide protection is dependent on a variety of factors, including the composition of the coating, service application, and the service conditions such as chemistry of the environment, amount of UV exposure, temperature, and relative humidity. Another important factor that determines the protective quality of the coating is the extent of damage caused by impact and abrasion during service. At present, maintenance cycles for commercial and military aircraft and ground vehicles, as well as engineered structures, is based on experience and appearance rather than a quantitative determination of coating integrity. Limitations to experience, variations in exposure conditions and the possibility of extensive corrosion damage occurring in hidden areas such as seams and lap joints are serious drawbacks to the present methodology used to determine maintenance schedules and results in considerable unnecessary costs. For example, it has been reported that the U.S. Air Force spends an average of $800M annually on corrosion control measures, of which coating maintenance operations are the majority (Cooke et al., 1998).

Monitoring the corrosion of engineered structures and vehicles has been proposed using a variety of corrosion sensors. The level of complexity of the proposed sensors varies from simple designs where the magnitude of either a galvanic or an impressed current is monitored over time to more advanced designs that incorporate multiple miniaturized electrodes including reference, chloride, and pH electrodes. The simple galvanic sensor design is robust and has been shown to be effective as time of wetness sensors and can be used to assess the corrosivity of the environment. Sensors with integrated reference, pH, and chloride ion selective electrodes can be used to measure corrosion rate and collect more detailed information on the variations in environment chemistry. While the ability to determine the condition of an existing coating over time would be beneficial in determining maintenance needs and possibly assessing early coating damage or degradation and preventing corrosion of the vehicle or structure, the present suite of sensors designed to detect corrosion and marketed to predicting the lifetime of the engineered components are not useful for determining the condition of the protective paint coatings.

A number of further attempts to monitor or measure the corrosion of engineered structures and vehicles are described in the following U.S. patent references.

U.S. Pat. No. 5,746,905 issued to Murray describes an invention for evaluating an organic coating using electrochemical impedance spectroscopy (EIS). EIS has been used to examine organic coatings in the manner generally described in Murray for some time. The structures and methods described in Murray do not, however, contemplate embedding the sensor system under the coating. In addition, the Murray disclosure requires three electrodes, one of which must be connected to the substrate. Finally, the Murray disclosure requires the use of a cell having a conductive interface with the coating.

U.S. Pat. No. 5,698,085 issued to Yu describes an invention to evaluate coating properties with a main focus on metallic coatings that corrode. Yu calls for the use of a test cell that is filled with a solution and requires electrical contact with the substrate for measurement.

U.S. Pat. No. 6,208,128 issued to Braconnier et al. describes a method for monitoring the loss of a refractory coating in a blast furnace. The Braconnier et al. disclosure describes at least two electrodes embedded under the refractory coating to make electrical measurements. The described system is directed to determining the loss of thickness in the refractory coating over time as opposed to organic coating degradation/defect detection and corrosion. The Braconnier et al. invention cannot be applied or modified to accomplish this latter type of degradation detection and monitoring. In addition, the electrodes utilized in the Braconnier et al. disclosure are consumed over time which complicates the long term consistency of the system since the response of the system is dependent on the length of the electrodes.

U.S. Pat. No. 4,839,593 issued to Spies describes a method for detecting the presence of corrosion through changes in an induced current arising from an electromagnetic pulse. The Spies disclosure does use radio frequency communication for instrument control and data acquisition. The method of measurement, however, is quite distinct and cannot be modified to monitor the performance of coatings in the long term. Furthermore, the specific structure disclosed in Spies is not directly embeddable in the coating.

U.S. Pat. No. 3,357,237 issued to Le Bel describes a method for monitoring the loss of material at a surface using ablation. This invention utilizes embedded electrodes and carries out electrical measurements. However, the type of electrical measurement being made monitors the loss of material as opposed to degradation of a coating. Thus, the physical properties measured and analyzed by Le Bel are distinct from the measurements and properties intended in the present invention.

U.S. Pat. No. 3,782,181 issued to Gurtler describes an invention similar in many respects to the Le Bel disclosure identified above. Gurtler involves a surface ablation sensor that is embedded under the surface to monitor the loss of materials over time.

In general the prior art fails to solve many of the problems associated with the monitoring of coating effectiveness for such structures as metallic sheets covered over with paint. In many instances in the above patents the coatings that are contemplated are thicker pipe jackets and the like with the measurements being directed to changes in the overall coating thickness at various locations. In addition, many of the systems described in the prior art require an electrical connection to the substrate as a basis for making electrical measurements characterizing the coating. Many systems in the prior art additionally fail to lend themselves to installation after placement of the coating and would be difficult to retrofit into an existing substrate/coating structure.

SUMMARY OF INVENTION

The present invention allows for the in-situ determination of the protectiveness of a coating system and monitoring of its subsequent failure through the use of an embedded electrode array. The sensor array of the present invention overcomes the limitations of previous attempts to measure coating integrity in that an electrical connection to the substrate material is not needed. The system is embedded underneath the coating and is sensitive to coating degradation prior to the onset of substrate corrosion. In addition, the sensor system does not itself adversely affect the performance of the coating system. Electrochemical impedance responses at three discrete frequencies are used in the preferred embodiment to determine the parameter N', defined as the product of the phase angle and the magnitude of the impedance. The system of the present invention can be fabricated using off the shelf components, integrated circuit fabrication methods and MEMS techniques.

DETAILED DESCRIPTION OF THE PREFERRED EMBODIMENTS

Two sensor designs are considered in the implementation of the system of the present invention. The first sensor structure consists of a system of pins that can either all be mounted and electrically isolated from the substrate panel or have one of the sensing pins in electrical contact with the substrate panel. In this configuration, both the protectiveness of the coating system and the presence of coating defects that result in exposure of bare metal can be detected. These pins are part of an integrated circuit package that has the needed components for data collection and communication incorporated. Power can be supplied through the use of a hard-wired source, on-board fuel cells or batteries, or through microwave transmission. A schematic diagram of the sensor mounted to a substrate is shown in FIG. 1a and is described in more detail below.

A second sensor structure consists of similar components but is much smaller in nature. In this case, it is fabricated using MEMS technology to enable miniaturization of the sensor such that it can be incorporated into the paint itself. In this case, no electrical contact between the sensor and the substrate is needed or generally desired. In this configuration, only the protectiveness of the coating system can be evaluated.

Figure 1A:
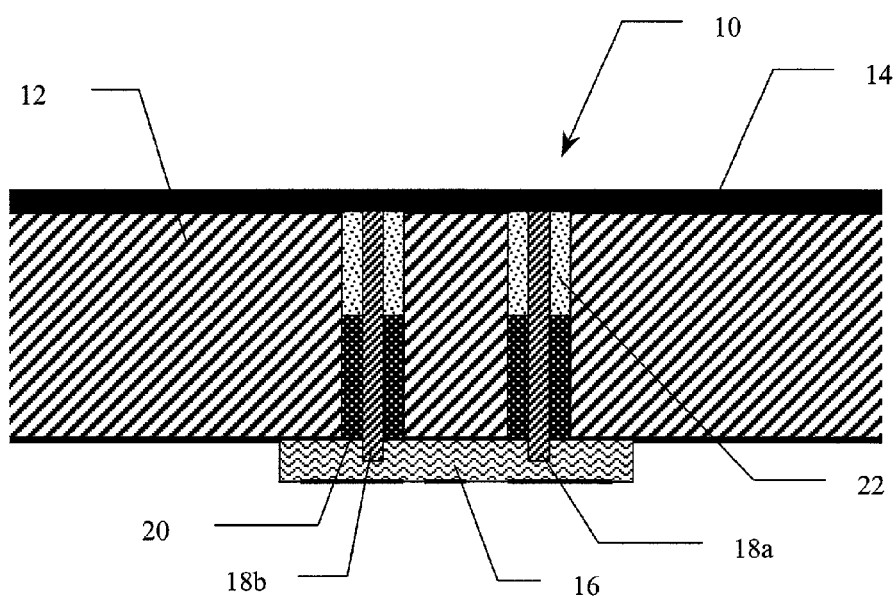
FIG. 1a is a detailed cross-sectional view of the implementation of a sensor of the present invention in conjunction with a substrate/coating structure.

FIG. 1a discloses in cross-section the first embodiment of a sensor of the present invention utilizing the system of pins mounted and electrically isolated from the substrate panel. FIG. 1a shows a single panel configuration of a sensor installation while FIG. 1b discloses the installation of a sensor on a lap joint such as is often encountered on aircraft skin panels, ship hull panels, etc.

In FIG. 1a, coated panel 10 is seen in cross-section as comprising substrate 12 and coating 14. Two apertures have been drilled in substrate 12, typically prior to the placement of coating 14 thereon. Within these apertures are positioned sensor electrodes 18a and 18b as shown. Electrodes 18a and 18b are positioned on integrated circuit 16 where they are connected to the balance of the sensor circuitry described in more detail below. Electrodes 18a and 18b are held centered in the apertures by means of insulating sleeves 20 that align electrodes 18a and 18b and effectively insulate them from electrical contact with substrate 12. Insulating epoxy 22 is used to fill in the balance of the apertures up to the top surface of substrate 12. The surface of substrate 12, as well as the top faces of electrodes 18a and 18b, along with the surrounding insulating epoxy 22, are sanded prior to placement of coating 14 there over.

Figure 1B:
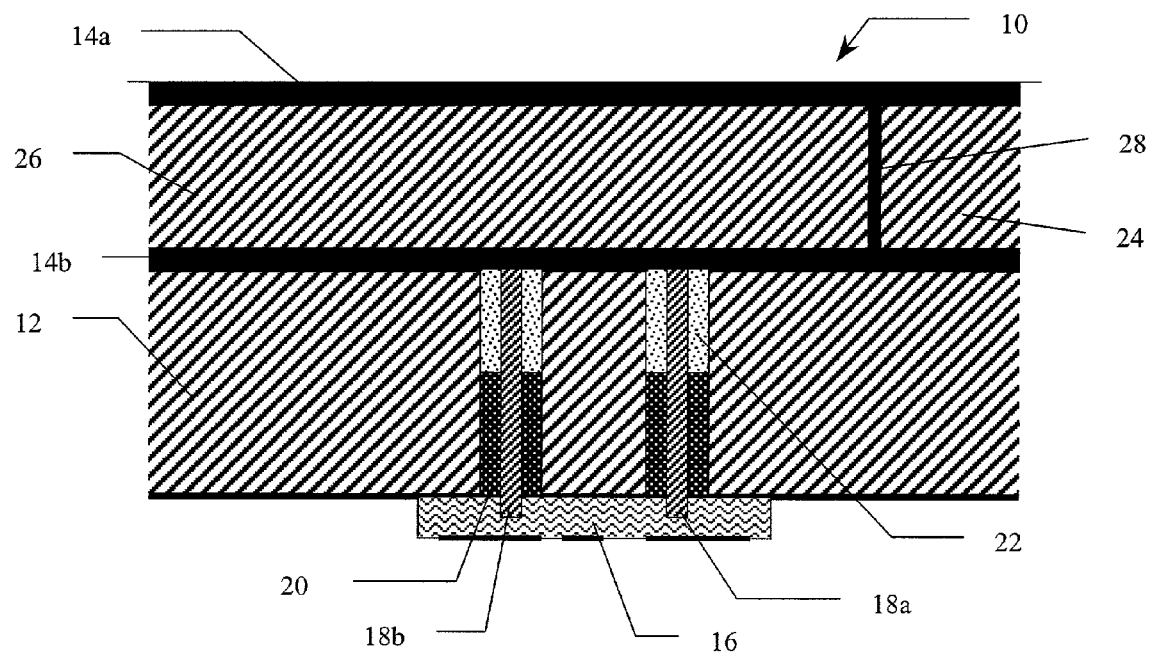
FIG. 1b is a detailed cross-sectional view of the implementation of the sensor of the present invention in conjunction with a lap joint substrate/coating structure.

FIG. 1b discloses a slightly modified application of the present invention to a lap joint configuration typical in aircraft skins and the like. In this configuration the sensor structure is the same, however, the manner of installation is slightly different. In this embodiment additional substrate sections 24 and 26 are placed over the primary substrate 12 to form a typical lap joint 28 where two panels may meet as on the skin of an aircraft. There are two coatings in this configuration that are subject to degradation, the outside coating 14a on the top substrates 24 and 26 and the secondary coating 14b over the lower substrate 12. The positioning of the sensor in FIG. 1b is such as to monitor the degradation of the intermediate coating 14b. It would be anticipated that other sensors would be mounted apart from the lap configuration so as to monitor the degradation and effectiveness of coating 14a.

Installation of the sensor shown in FIG. 1b, likewise involves the drilling of apertures in the lower substrate 12 and the positioning of the sensor from the backside of substrate 12 as shown. While installation of the sensor could certainly occur when the lap joint is open, such as prior to construction of the joint, it is also possible to install the sensor after the lap joint has been assembled. Appropriate drilling techniques could easily position the sensor from the backside of substrate 12 without significantly intruding into the intermediate coating 14b.

Monitoring the condition of the coating based upon data gathered by the sensor can be carried out through upper substrates 24 and 26 just as with the data interrogation methods described below in conjunction with a single substrate configuration.

Figure 4:
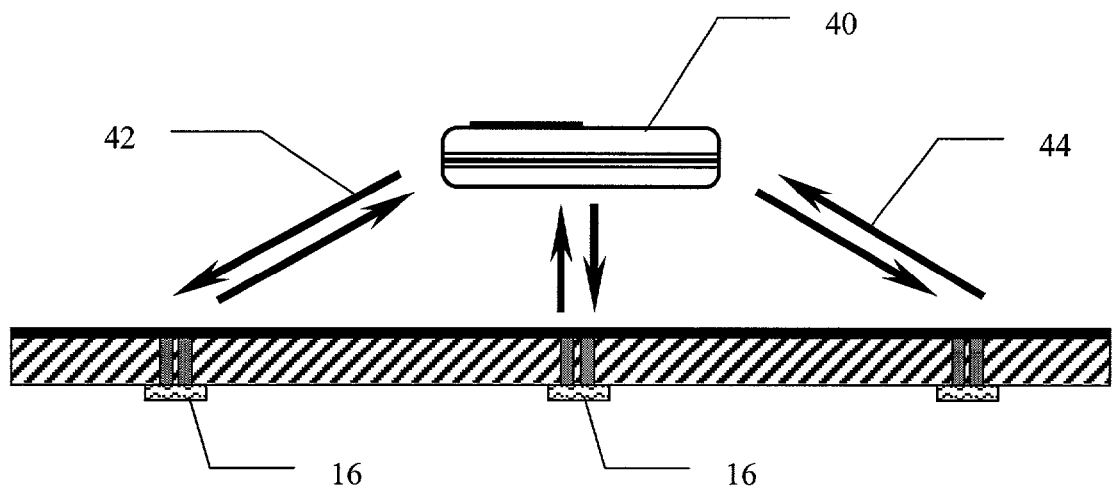
FIG. 4 is a partial cross-sectional view of the implementation of the system of the present invention detailing the wireless interrogation of the sensors.

Reference is now made to FIG. 4 for a brief description of the broader structure of the system of the present invention and the methods associated with its use. In FIG. 4 a schematic representation of the basic components of the system is shown. In this diagram the objects are not to scale but are presented primarily to reference their functional relationship. Substrate 12 is provided with a coating 14 much in the manner described in FIG. 1a above. Sensor circuits 16 along with the associated electrodes placed through apertures in substrate 12 are positioned at a variety of locations under the coated substrate. Data interrogation device 40 is utilized in conjunction with these "passive" sensors 16 to both trigger their operation and to receive a response in the form of transmitted data.

In the preferred embodiment data interrogation device 40, the components of which are described in more detail below, may be a hand-held device that is passed over the coated substrate surface and progressively interrogates each of the sensors embedded within the substrate. The process of the interrogation includes an initial transmission 42 from the data interrogation device 40 to the sensor 16 that serves to trigger the transmission 44 of data from the sensor 16 back to the data interrogation device 40. Likewise as discussed above, it is anticipated that the power source for the operation of sensor 16 could come from the data interrogation device 40 itself at the same point in the process where a response from the sensor is triggered. In other words, electromagnetic transmissions from the data interrogation device 40 could serve to both power the sensor 16 and trigger its data transmission response.

A number of mechanisms and methods are available to individually select specific sensors for interrogation. Each sensor might be discreetly identified by a transmission code that would precede the data telemetry itself. In addition to this discreet identification code, however, selective interrogation of the sensors could be carried out by variations in the frequency of the interrogation signals transmitted from the data interrogation device. As discussed elsewhere herein, a variety of sensor frequencies are utilized to increase the reliability of the data associated with the measurements of resistivity and capacitance for the coating. Similar variations in signal frequency would permit not only the discreet interrogation of a single sensor at a time but also the acquisition of signal data associated with a variety of sensor frequencies in support of the goal of greater data reliability.

Figure 5:
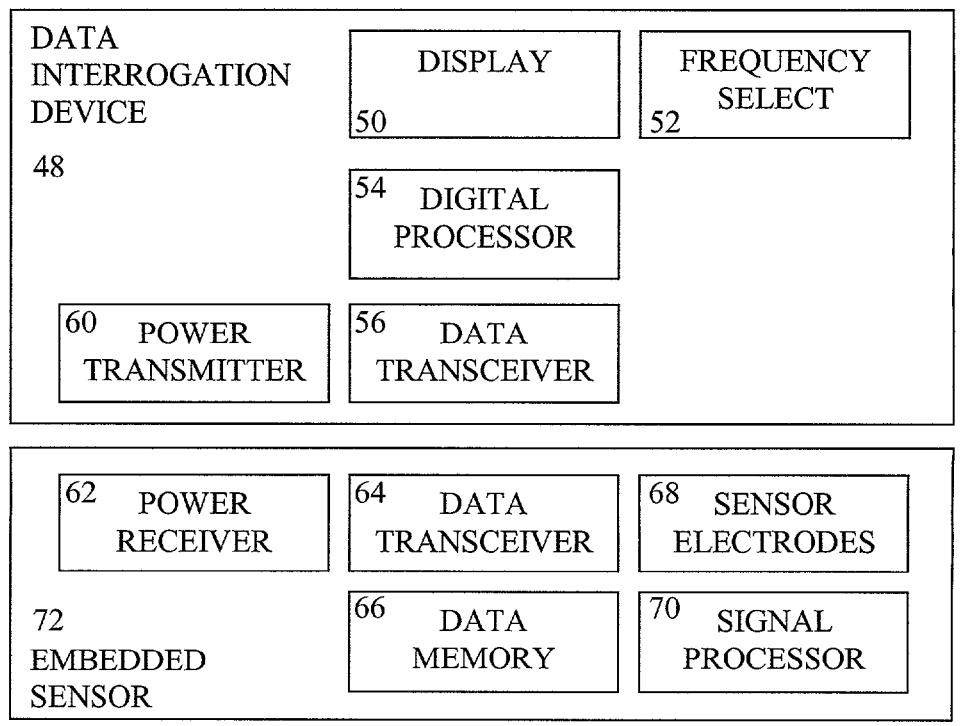
FIG. 5 is a schematic block diagram showing the various electronic components of the interrogation device and the embedded sensors of the present invention.

Detailed block diagrams of both the typical data interrogation device 48 and the typical embedded sensor 72 are shown in FIG. 5. The components of the data interrogation device 48 are generally well known in the art, not only with regard to their individual features but also with regard to their use as a wireless telemetry data transfer system. The user of the data interrogation device 48 would require access to display 50 in order to appropriately identify the conclusion as to coating integrity that the processing system reaches. Digital processor 54 within data interrogation device 48 makes this determination by receiving the data from data transceiver 56 which in turn receives it from the sensors. As mentioned above, it is anticipated that in the preferred embodiment, data interrogation device 48 would also incorporate a power transmitter 60 to direct and power up the individual sensors as the interrogation device comes into close proximity. Finally, a mechanism for frequency selection 52, is incorporated into interrogation device 48 in order to permit the user (or the system programming if automated) to progressively select a variety of frequencies in order to achieve the purposes discussed above.

Embedded sensor 72, in addition to being structurally configured as described above with regard to FIGS. 1a and 1b, incorporates a number of basic and known in the art electronic elements. Power receiver 62 is configured to receive the electromagnetic waves from power transmitter 60 and to relay this minimal necessary power to the balance of the electronic components of the sensor system. Data transceiver 64 may simply be a transmission device appropriate for directing data from the sensor to the interrogation device at radio frequencies or the like. While the present invention anticipates a triggering signal from the data interrogation device, such a signal may simply be the receipt of the power transmission discussed immediately above. Such activation of the embedded sensor 72 would be sufficient to trigger a transmission from data transceiver 64. In other words, data transceiver 64, in an alternative preferred embodiment may simply be a data transmitter with no receiving circuits required.

Sensor electrodes 68 are, of course, incorporated into the embedded sensor as discussed above with regard to FIG. 1a. The impedance response values from sensor electrodes 68 are conducted to signal processor 70 wherein the impedance values and phase angle values may be digitized and stored in data memory 66.

Alternate to the above, the processing that might otherwise occur in the data interrogation device could occur in the circuitry of the embedded sensor with the appropriate signal processing circuitry provided. It is anticipated, however, that it becomes more cost efficient to provide processing power at the interrogation device as opposed to each of the embedded sensors.

Once stored in data memory 66, information regarding the coating characteristics may be transmitted from data transceiver 64 to the data interrogation device upon prompting as described above. As an alternative to the mechanism for storing the data on board the embedded sensor, the triggering of the embedded sensor by the receipt of a power transmission from the data interrogation device could simply trigger a sensor reading whose signal data is immediately processed and configured for transmission directly to the data interrogation device. In other words, the embedded sensor would not retain such coating characteristic data on board and would only acquire such data about the coating upon being prompted by the data interrogation device.

One benefit to retaining some type of memory device on board the sensor could be the acquisition and retention of time dependent data regarding the coating characteristics.

Figure 6:
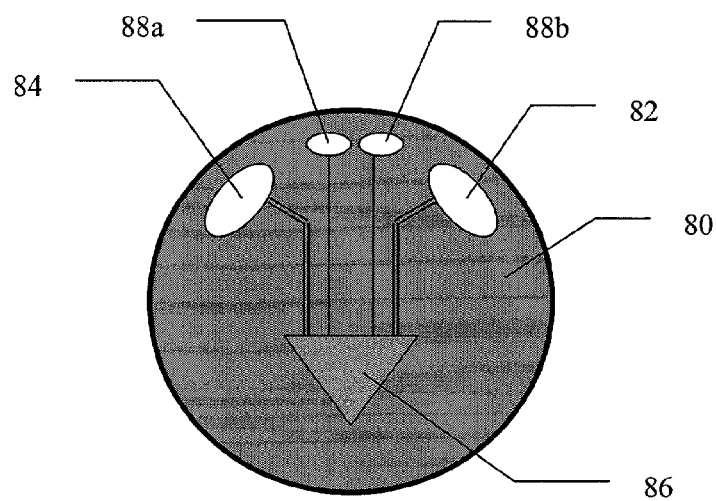
FIG. 6 is a detailed side view of a microsphere embodiment of a sensor of the present invention.
Figure 7:
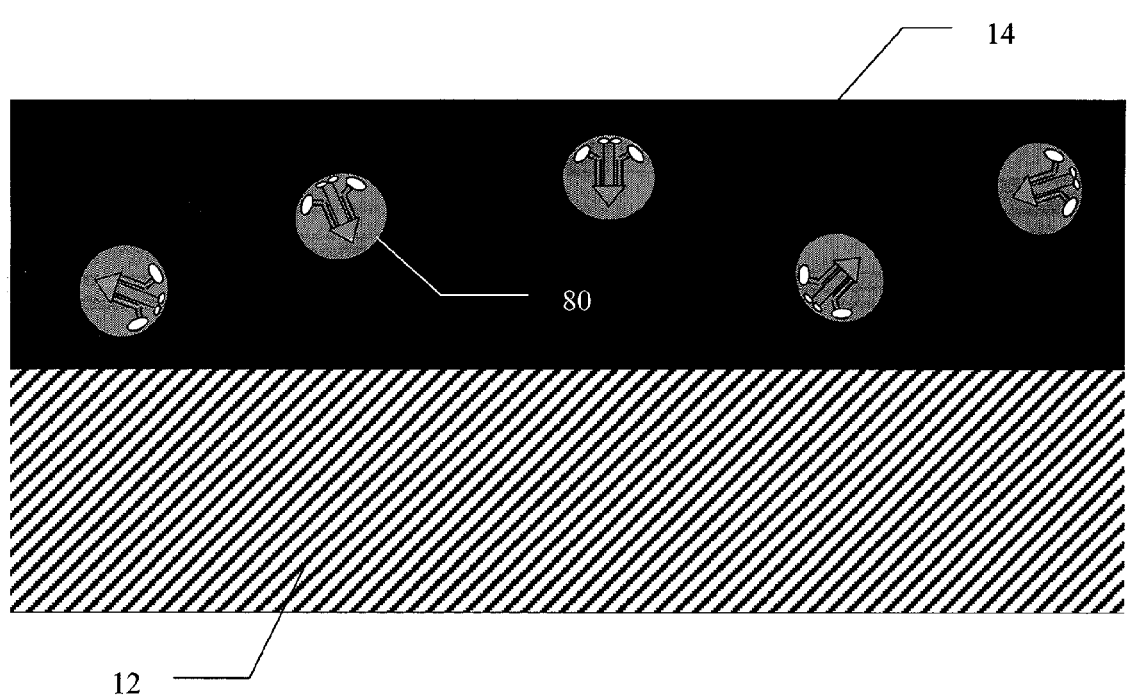
FIG. 7 is a detailed cross-sectional view of the microsphere sensor implementation in conjunction with a substrate/coating structure.

Reference is now made to FIGS. 6 and 7 for a brief description of an alternative embodiment of the sensor structure of the present invention. Insofar as the preferred sensor structure has been identified as one involving wireless telemetry, the actual size, shape and configuration of the sensor is highly variable. One type of electronic packaging technology that has gained favor in recent years with its ability to package electronic systems in small and relatively inexpensive structures, has been spherical semiconductor technology. Examples of this technology and its wide applicability can be found in the disclosures contained in U.S. Pat. No. 6,004,396 issued to Ishikawa on Dec. 21, 1999 entitled Spherical Shaped Semiconductor Integrated Circuit, U.S. Pat. No. 6,052,517 issued to Matsunaga et al. on Apr. 18, 2000 entitled Spherical Cell Design for VLSI Circuit Design on a Spherical Semiconductor, and U.S. Pat. No. 6,195,789 issued to Matsunaga on Feb. 27, 2001 entitled Method for Circuit Design on a Spherical Semiconductor Having Critical Dimensions. All of the above patents referenced are owned by Ball Semiconductor, Inc. of Allen, Tex. and the disclosures of each are incorporated herein by reference in their entirety.

FIG. 6 shows in schematic form a configuration for a microsphere semiconductor device that incorporates the necessary components for a sensor of the present invention. In FIG. 6 microsphere sensor 80 incorporates a power receiver conductive element 82 as well as a data transceiver conductive element 84. Element 82 would of course serve to receive an electromagnetic wave transmission from the interrogation device in a manner that would activate the sensor and prompt the transmission of data. Element 84 would provide the source of the telemetry transmission to the data interrogation device.

Electrodes 88a and 88b would be positioned in such a manner as to be directly exposed to the coating which, as described in more detail below, completely surrounds the sensor in this embodiment. The balance of the electronics are positioned at 86 and include all of the elements described above with respect to FIG. 5. Various techniques are known in the art for etching or establishing the necessary semiconductor paths on a silicon microsphere or similarly composed spherical semiconductor. The size of the semiconductor microsphere and this embodiment is driven primarily by the coating requirements and the likelihood that a sphere of a given size would significantly disrupt the surface characteristics of the object being coated.

In FIG. 7, a cross-sectional view of a typical substrate/coating structure is shown. Although not necessarily to scale, the diagram indicates that a plurality of microspherical semiconductors could easily be embedded within the layer of coating 14 in such a way as to remain responsive to the degradation of the coating 14 and at the same time remain responsive to interrogation by a data interrogation device of the type described with regard to FIGS. 4 and 5.

It is anticipated that the distribution of sensors 80 within coating 14 over substrate 12 could vary significantly according to the specific application involved. In some instances it may be desirable to have a dense array of sensors 80, in some environments operating at a variety of frequencies, such that relatively localized characterizations of the coating can be made. In other environments a very sparse density may be appropriate and fully adequate to monitor the degradation of the coating on the substrate involved.

The basic sensor design concept has been shown to be able to detect differences in coatings as well as the presence of coating defects. In testing operations, four coating systems were examined: a three-coat polyurethane, a one-coat polyurethane, a one-coat polyurethane in which the surface was contaminated with hydraulic fluid (as could occur in a variety of situations), and a one-coat enamel. In addition, three defect geometries were considered using the three-coat polyurethane system: no defect, a ~1 mm diameter pinhole, and a ~1×50 mm scribe. These coatings and the sensor response were evaluated as a function of time when exposed to a daily three minute 5% NaCl salt spray followed by a 55° C., 80–90% RH soak for the remainder of the 24 hour period. Based on an examination of currently used appliqué coatings used by the U.S. Air Force, a N' value of $10^8$–$10^9$ was considered to be highly protective. N' values in the range of $5\times10^6$ to $10^8$ were considered marginal coatings and N' values less than $5\times10^6$ were considered poor. Defects were considered detected when N' was less than $10^8$.

Figure 2:
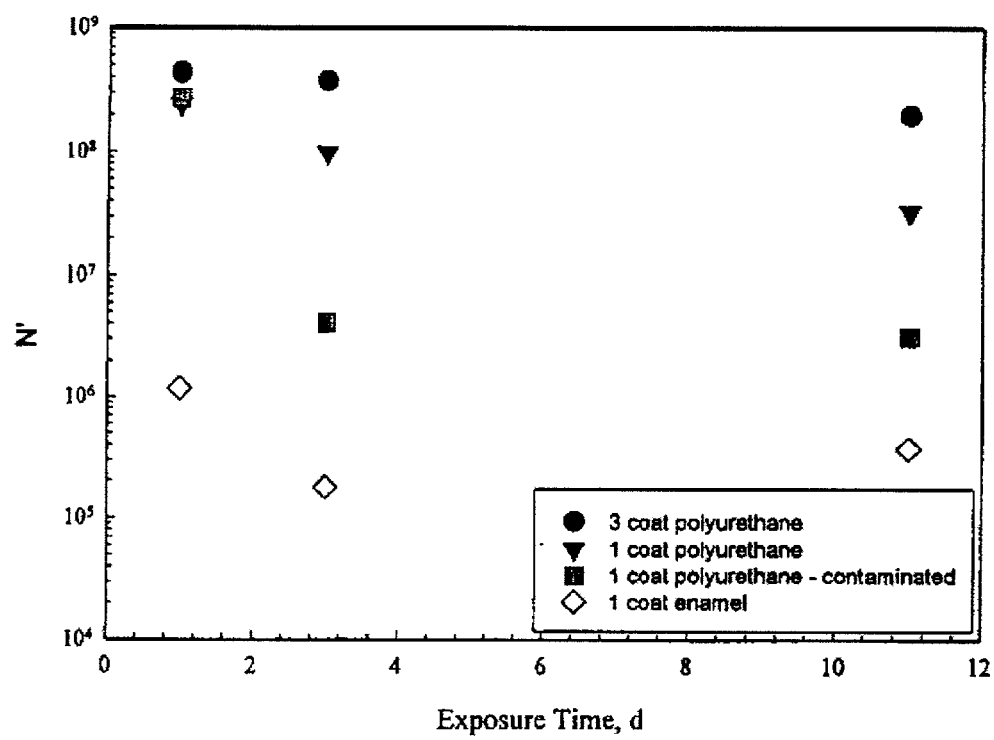
FIG. 2 is a graphic plot of the parameter N' versus exposure time for a number of different coatings.
Figure 3:
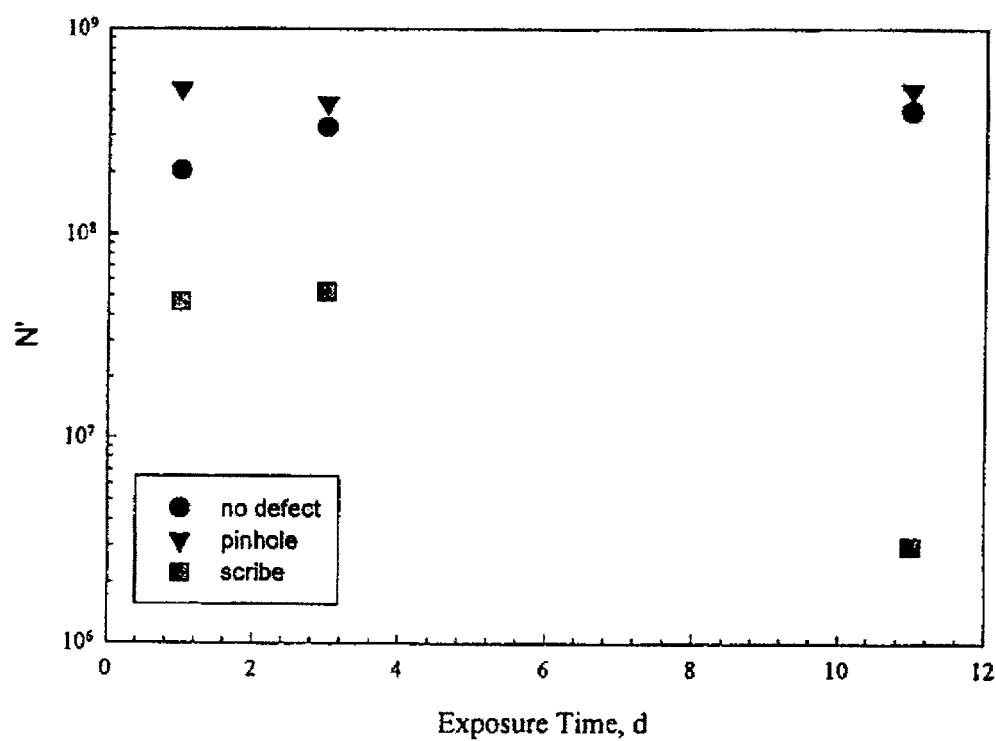
FIG. 3 is a graphic plot of the parameter N' versus exposure time for a number of different types of degradation features.

The three-coat polyurethane was noted to be protective with N'>$10^8$ even after eleven days exposure (FIG. 2). The one-coat polyurethane was initially protective, but after eleven days was found to be only marginally protective. The contaminated one-coat polyurethane system was easily discernable from the standard one-coat polyurethane coating, with N' initially being high but decreasing rapidly to ~$4\times10^6$ after three days. For the one-coat enamel, the sensor showed N' values of between $10^5$ and $10^6$ for the entire testing period. These results were in line with visual observation of the coating performance after testing which showed considerable corrosion product deposition on the panel surface in the case of the one-coat enamel system. For the three-coat polyurethane coating with and without defects (FIG. 3), the scribe was detected initially after 1 day of exposure, however the pin hole was not detected even after eleven days of exposure. These results are somewhat in line with a visual inspection of the panels with the pinhole not experiencing any measurable coating creep back and nearly 3 mm of creep back observed along the scribe length.

This sensor design concept of the present invention can therefore distinguish between coatings of different protectiveness and can detect the presence of coating defects. In addition, unlike other sensor designs that are mounted to an outside surface or that sometimes cause the corrosion they are trying to detect, the current sensor is mounted underneath the coating and does not cause the onset of coating failure nor does it accelerate corrosion by its presence.

In summary, the system of the present invention consists of non-corrodible electrodes embedded in an insulating matrix with the following characteristics:

Sensors can be embedded under coatings in areas of limited access and mounted to a substrate panel to measure coating integrity and the presence of coating defects.

Sensors can be incorporated into coatings and used to measure coating integrity without making electrical contact to the substrate.

Sensors do not adversely effect coating system performance.

The system as a whole does not cause corrosion of the substrate.

The system can detect coating degradation prior to the onset of corrosion.

Communication and data throughput can be achieved using RF telemetry, hard link connections, or IR data link connections as well as other such wireless or wired data communication methods.

Power can be obtained using RF/microwave transmission as well as on-board fuel cells or batteries or other known power supply devices.

The system can detect onset of coating degradation prior to the onset of substrate degradation.

The system utilizes electrochemical impedance spectroscopy at three frequencies and coating performance and defect detection are determined using a nominal parameter N'.

We claim:

1. A system for monitoring the effectiveness of a coating on a substrate surface, the system comprising:
   (a) a sensor array positioned in contact with said coating, said sensor array comprising:
      (i) a plurality of sensor pins in contact with said coating;
      (ii) at least one sensor circuit connected across at least two of said sensor pins, said sensor circuit comprising signal generation circuitry for generating an electromagnetic signal across said at least two sensor pins, response signal metering circuitry for measuring a response electromagnetic signal across said at least two sensor pins, and first telemetry circuitry; and
      (iii) at least one power supply circuit; and
   (b) a data interrogation device positioned in proximity to said sensor array, said interrogation device comprising second telemetry circuitry for data communication with said first telemetry circuitry of said sensor array.

2. The system of claim 1 wherein said at least one sensor circuit of said sensor array further comprises digital signal processing circuitry.

3. The system of claim 1 wherein said plurality of sensor pins are electrically insulated from said substrate.

4. The system of claim 1 wherein at least one of said plurality of sensor pins is electrically connected to said substrate.

5. The system of claim 1 wherein said sensor array comprises a plurality of discrete sensor packages, each of said sensor packages comprising at least two of said plurality of sensor pins, one of said sensor circuits, and one of said power supply circuits, said plurality of discrete sensor packages arranged in an ordered matrix in contact with said coating.

6. The system of claim 1 wherein said plurality of sensor pins are arranged in an ordered matrix in contact with said coating and are each connected to a single one of said sensor circuits.

7. The system of claim 6 wherein said plurality of sensor pins are discretely connected in parallel to said sensor circuit.

8. The system of claim 6 wherein said plurality of sensor pins are connected in at least one series circuit with said sensor circuit.

9. The system of claim 1 wherein said first telemetry circuitry and said second telemetry circuitry each comprise radio frequency wireless telecommunication circuits.

10. The system of claim 1 wherein said first telemetry circuitry and said second telemetry circuitry each comprise infrared signal wireless telecommunication circuits.

11. The system of claim 1 wherein said first telemetry circuitry and said second telemetry circuitry each comprise hard wired data telecommunication circuits.

12. The system of claim 1 wherein said at least one power supply circuit comprises an on-board electrical fuel cell.

13. The system of claim 1 wherein said at least one power supply circuit comprises an electromagnetic wave receiver and said data interrogation device further comprises an electromagnetic wave transmitter, power to said sensor array being transmitted from said interrogation device.

14. The system of claim 5 wherein said discrete sensor packages are dispersed within said coating and are generally insulated electrically from said substrate surface.

15. The system of claim 14 wherein said discrete sensor packages each comprise a spherical shaped semiconductor device, wherein said sensor pins comprise exposed contact surfaces on said semiconductor device and said at least one sensor circuit and said at least one power supply circuit comprise semiconductor integrated circuits.

16. The system of claim 15 wherein said spherical shaped semiconductor device comprises a silicon based microsphere capable of being incorporated into the coating material prior to or during application to said substrate.

17. A system for monitoring the effectiveness of a coating on a substrate surface, the system comprising:
(a) a sensor array positioned in contact with said coating and proximate to said substrate surface, said sensor array comprising a plurality of discrete sensor packages, each of said sensor packages comprising:
(i) a plurality of sensor pins in contact with said coating electrically insulated from said substrate;
(ii) a sensor circuit connected across at least two of said sensor pins, said sensor circuit comprising signal generation circuitry for generating an electromagnetic signal across said at least two sensor pins, response signal metering circuitry for measuring a response electromagnetic signal across said at least two sensor pins, digital signal processing circuitry, data storage circuitry and first telemetry circuitry, said first telemetry circuitry comprising radio frequency wireless telecommunication circuitry; and
(iii) at least one power supply circuit, said at least one power supply circuit comprising an electromagnetic wave receiver; and
(b) a data interrogation device positioned in proximity to said sensor array, said interrogation device comprising second telemetry circuitry for data communication with said first telemetry circuitry of said sensor array, said second telemetry circuitry comprising radio frequency wireless telecommunication circuitry, said data interrogation device further comprising an electromagnetic wave transmitter, wherein power to said sensor array is wirelessly transmitted from said interrogation device to said at least one power supply circuit.

18. A method for monitoring the effectiveness of a coating on a substrate surface, the method comprising:
positioning a sensor array within said coating and proximate to said substrate surface;
generating an interrogating electrical signal and directing it into said coating from said sensor array;
measuring electrical impedance by measuring signal magnitude and phase angle values from said interrogating electrical signal, wherein said signal magnitude is indicative of the resistivity of said coating and said phase angle is indicative of the capacitance of said coating; and
multiplying said impedance magnitude and phase angle values to establish a nominal parameter N', the magnitude of said nominal parameter N' providing a direct indication of the resistance and capacitance of said coating and therefore of the effectiveness of said coating on said substrate surface.

19. The method of claim 18 further comprising the steps of:
retaining said measured impedance data in at least one signal storage device positioned in conjunction with said sensor array;
positioning a data interrogation device in proximity to said at least one signal storage device; and
transferring said measured impedance data from said signal storage device to said data interrogation device.

20. The method of claim 19 wherein said step of transferring said measured impedance data comprises wirelessly transmitting a radio frequency signal from said signal storage device to said data interrogation device.

21. The method of claim 19 wherein said step of transferring said measured impedance data comprises wirelessly transmitting an infrared signal from said signal storage device to said data interrogation device.

22. The method of claim 19 wherein said step of transferring said measured impedance data comprises transmitting an electrical signal from said signal storage device to said data interrogation device across a hardwired connection.

23. The method of claim 18 further comprising the step of providing a power source for said sensor array.

24. The method of claim 23 wherein said step of providing a power source comprises providing a battery in direct association with said sensor array.

25. The method of claim 19 further comprising the step of providing a power source for said sensor array.

26. The method of claim 25 wherein said step of providing a power source comprises providing a battery in direct association with said sensor array.

27. The method of claim 25 wherein said step of providing a power source comprises transmitting an electromagnetic wave from said data interrogation device to said sensor array.

28. The method of claim 18 wherein said step of generating an interrogating electrical signal comprises generating an AC signal and said step of measuring electrical impedance data comprises measuring such data at a plurality of distinct signal frequencies.

29. The method of claim 28 wherein said measurement of impedance data is carried out for at least three distinct frequencies.

30. A method for monitoring the effectiveness of a coating on a substrate surface, the method comprising:

positioning a sensor array within said coating and proximate to said substrate surface;

generating an interrogating AC electrical signal and directing it into said coating from said sensor array;

measuring electrical impedance by measuring signal magnitude and phase angle values from said interrogating electrical signal at a plurality of distinct frequencies;

retaining said measured impedance data in at least one signal storage device positioned in conjunction with said sensor array;

positioning a data interrogation device in proximity to said at least one signal storage device;

providing a power source for said sensor array by wirelessly transmitting an electromagnetic wave from said data interrogation device to said sensor array;

transferring said measured impedance data by wirelessly transmitting a radio frequency signal from said signal storage device to said data interrogation device; and multiplying said impedance magnitude and phase angle values to establish a nominal parameter N, the magnitude of said nominal parameter N providing a direct indication of the effectiveness of said coating on said substrate surface.

* * * * *